(12) United States Patent
Brady et al.

(10) Patent No.: US 6,797,004 B1
(45) Date of Patent: Sep. 28, 2004

(54) HOLDERS FOR INTRAOCULAR LENSES

(75) Inventors: Daniel G. Brady, San Juan Capistrano; Robert Glick, Lake Forrest, both of CA (US)

(73) Assignee: Advanced Medical Optics, Inc., Santa Ana, CA (US)

(*) Notice: Subject to any disclaimer, the term of this patent is extended or adjusted under 35 U.S.C. 154(b) by 0 days.

(21) Appl. No.: 09/517,229

(22) Filed: Mar. 2, 2000

(51) Int. Cl.⁷ .................................................. A61F 2/16
(52) U.S. Cl. .................. 623/6.4; 623/6.38; 623/6.39
(58) Field of Search .............................. 623/6.11, 6.32, 623/6.34, 6.37, 6.38, 6.39, 6.4

(56) References Cited

U.S. PATENT DOCUMENTS

| | | | |
|---|---|---|---|
| 4,253,199 A | | 3/1981 | Banko |
| 4,254,509 A | | 3/1981 | Tennant |
| 4,409,691 A | | 10/1983 | Levy |
| 4,790,847 A | | 12/1988 | Woods |
| 4,842,601 A | | 6/1989 | Smith |
| 4,888,012 A | | 12/1989 | Horn et al. |
| 4,888,015 A | | 12/1989 | Domino |
| 4,888,016 A | * | 12/1989 | Langerman ................ 623/6.39 |
| 4,892,543 A | | 1/1990 | Turley |
| 4,932,966 A | | 6/1990 | Christie et al. |
| 4,932,968 A | | 6/1990 | Caldwell et al. |
| 4,976,732 A | | 12/1990 | Vorosmarthy |
| 4,994,082 A | | 2/1991 | Richards et al. |
| 5,019,098 A | | 5/1991 | Mercier |
| 5,171,266 A | | 12/1992 | Wiley et al. |
| 5,173,723 A | | 12/1992 | Volk |
| 5,275,623 A | | 1/1994 | Sarfarazi |
| 5,354,335 A | | 10/1994 | Lipshitz et al. |
| RE34,998 E | * | 7/1995 | Langerman ................ 623/6.39 |
| 5,443,506 A | | 8/1995 | Garabet |
| 5,476,514 A | | 12/1995 | Cumming |
| 5,489,302 A | | 2/1996 | Skottun |
| 5,496,366 A | | 3/1996 | Cumming |
| 5,562,731 A | | 10/1996 | Cumming |
| 5,578,081 A | | 11/1996 | McDonald |
| 5,593,436 A | * | 1/1997 | Langerman ................ 623/6.38 |
| 5,628,795 A | | 5/1997 | Langerman |
| 5,674,282 A | | 10/1997 | Cumming |
| 5,814,103 A | | 9/1998 | Lipshitz et al. |
| 5,824,074 A | * | 10/1998 | Koch ........................ 623/6.34 |
| 5,876,442 A | | 3/1999 | Lipshitz et al. |

FOREIGN PATENT DOCUMENTS

| | | |
|---|---|---|
| DE | 4038088 | 6/1992 |
| EP | 0507292 | 10/1992 |

OTHER PUBLICATIONS

Thornton, Accommodation In Pseudophakia, 25, pp. 159–162.
Video Tape "New Elliptical Acco. IOL For Cataract Surgery", Shown at ASCRS Symposium on Apr. 10, 1999. (Video Enclosed).
Partial Program re: ASCRS Symposium, Showing Video Tape Shown Between Apr. 10–14, 1999.

* cited by examiner

Primary Examiner—Dinh X. Nguyen
(74) Attorney, Agent, or Firm—Stout, Uxa, Buyan & Mullins, LLP; Frank J. Uxa; Peter Jon Gluck

(57) ABSTRACT

An intraocular lens system including one or more intraocular lenses (IOL) and a peripheral holder. The peripheral holder is configured to receive and retain the distal end of a fixation member of the IOL and provide a dynamic interface between the natural capsular bag and fixation member. The holder is preferably annular and flexible and transmits movement of the capsular bag from the surrounding ciliary muscles to the IOL. In this manner, a circumferential surface contact with the capsular bag is provided and accommodation of the IOL is improved. If two IOLs are received in the holder, a spacer may be provided to insure consistent spacing between the IOLs. Alternatively, an IOL system may include two IOLs and a spacer, without the holder. The holder desirably includes a sharp exterior corner to inhibit cell growth and posterior capsular opacification.

46 Claims, 4 Drawing Sheets

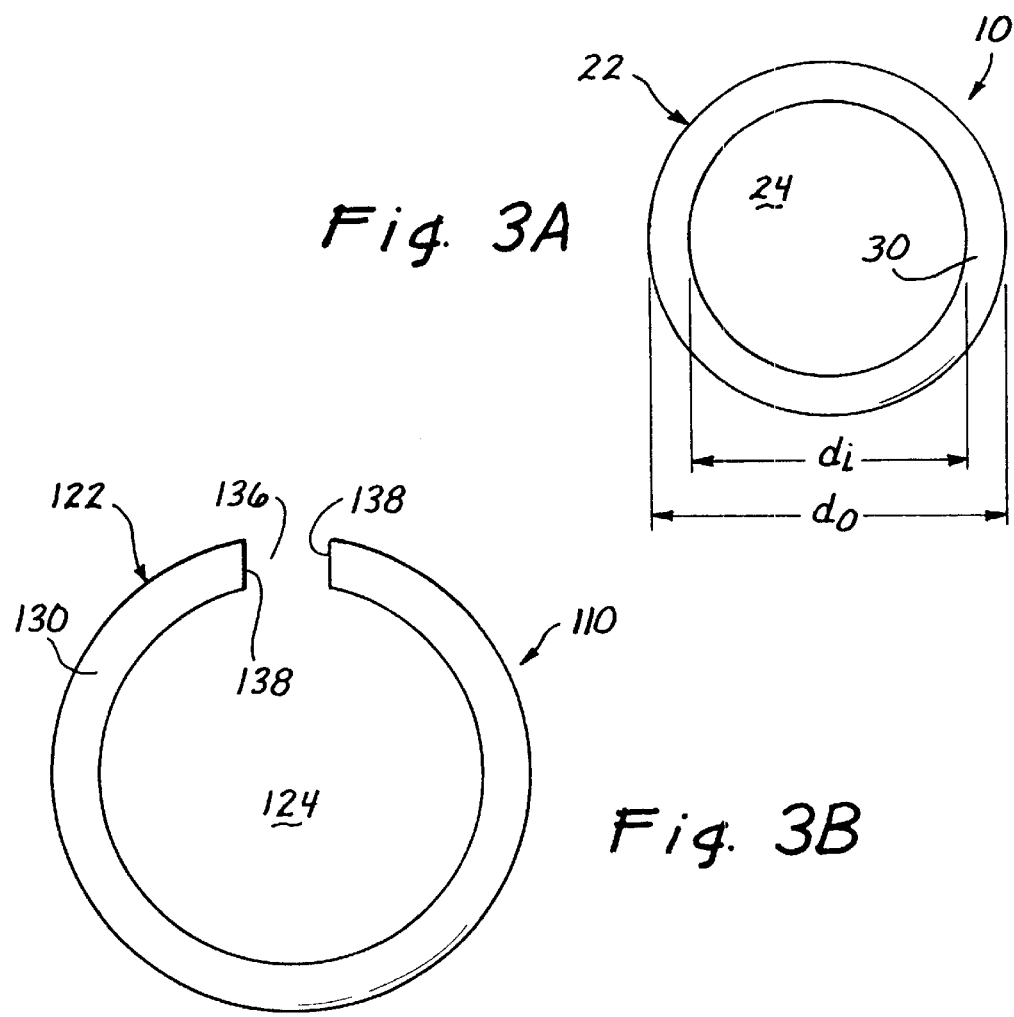
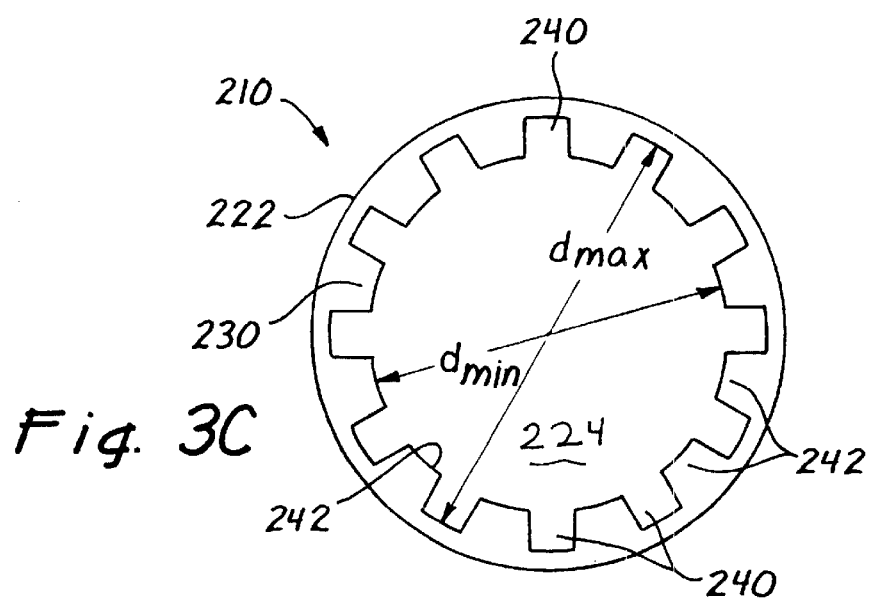

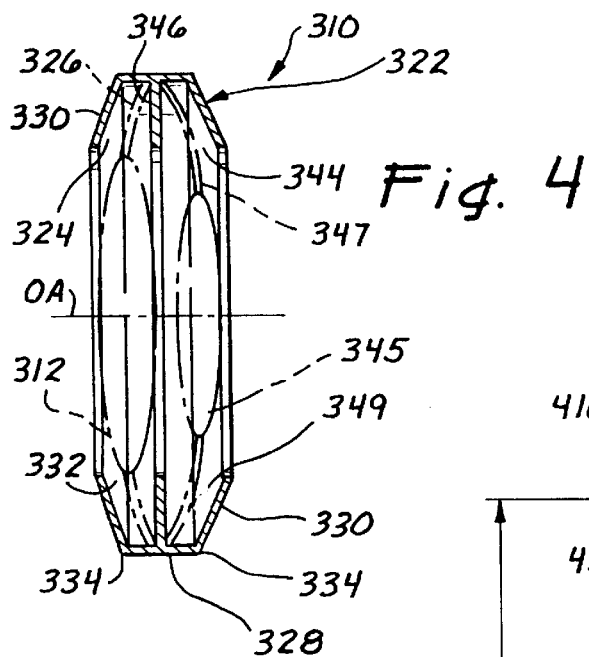
Fig. 4
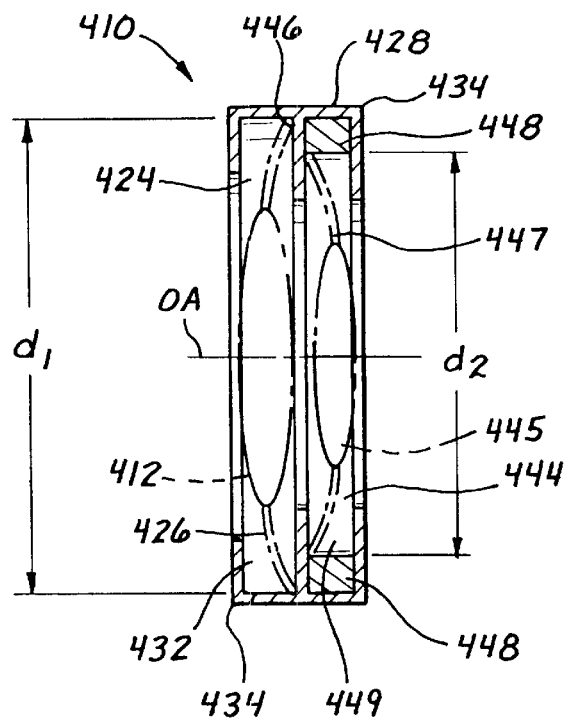
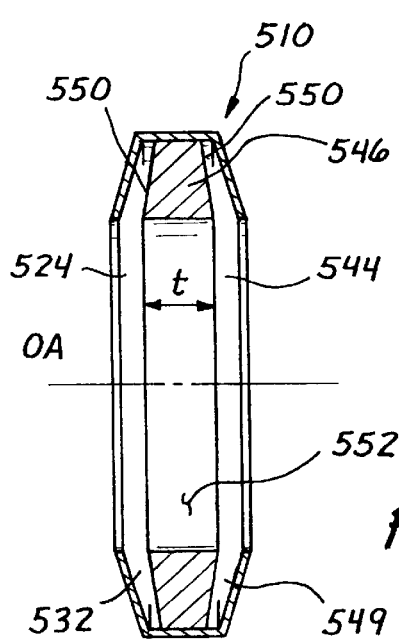
Fig. 5
Fig. 6

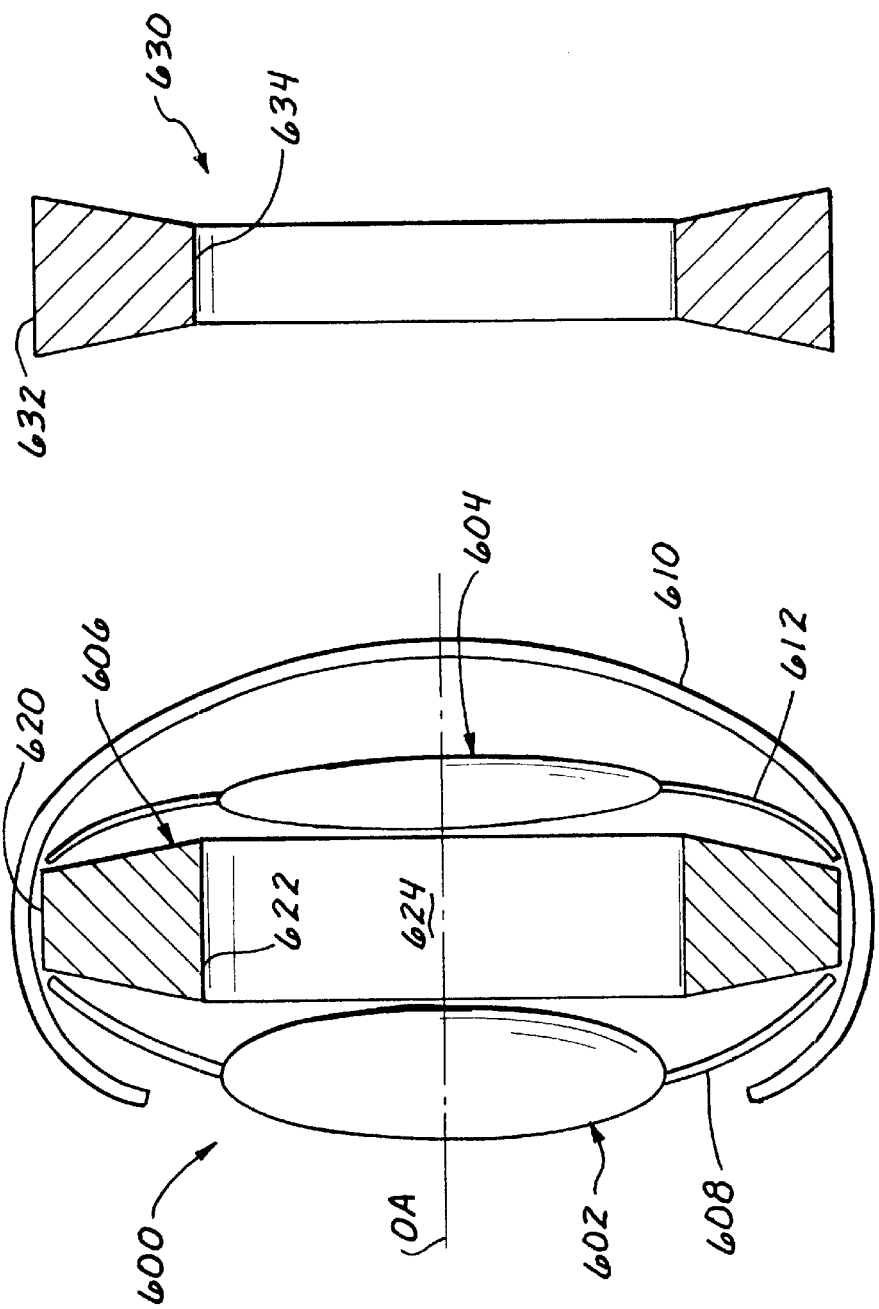

HOLDERS FOR INTRAOCULAR LENSES

BACKGROUND OF THE INVENTION

The present invention relates to intraocular lenses (IOLs). More particularly, the present invention relates to IOLs which are adapted to provide accommodating movement in the eye.

The human visual system includes the eyes, the extraocular muscles which control eye position within the eye socket, the optic and other nerves that connect the eyes to the brain, and particular areas of the brain that are in neural communication with the eyes. The visual system is particularly well adapted for the rapid and precise extraction of spatial information from a field of view, by analyzing the continuously changing patterns of radiant flux impinging upon the surfaces of the eyes.

Image formation is greatly complicated by the movement of the eyes within the head, as well as by the movement of both eyes and the head relative to the external sea of radiant energy. Visual input is ordinarily sampled by discrete momentary pauses of the eyes called fixations, interrupted by very rapid ballistic motions known as saccades which bring the eye from one fixation position to the next. Smooth movements of the eyes can occur when viewing an object having a predictable motion.

Each eye forms an image upon a vast array of light sensitive photoreceptors of the retina. The outer cover of the eye, or cornea, protects the lens and acts as a colorless filter to refract light onto the iris and pupil. The iris corresponds to the aperture in a camera and contains muscles which alter the size of the pupil to control the amount of light that enters the eye. The crystalline lens located just behind or posterior to the pupil has a variable shape under the indirect control of the peripheral ciliary muscles. Having a refractive index higher than the surrounding media, the crystalline lens gives the eye a variable focal length, allowing accommodation to objects at varying distances from the eye.

Much of the remainder of the eye is filled with fluids and materials under pressure which help the eye maintain its shape. For example, the aqueous humor fills the anterior chamber between the cornea and the iris, and the vitreous humor fills the majority of the volume of the eye in the vitreous chamber located between the lens and the retina. The crystalline lens is contained within a third chamber of the eye, the posterior chamber, which is positioned between the anterior and vitreous chambers.

The human eye is susceptible to numerous disorders and diseases, a number of which attack the crystalline lens. For example, cataracts mar vision through cloudy or opaque discoloration of the lens of the eye. Cataracts often result in partial or complete blindness. If this is the case, the crystalline lens can be removed and replaced with an intraocular lens, or IOL.

While restoring vision, conventional monofocal IOLs have only limited or substantially no ability for accommodation (i.e., the focusing on near objects). To overcome this lack of accommodation, a patient may be prescribed eyeglasses. Alternative attempts in the art involve enhancing the accommodation ability of IOLs. Accommodation may be accomplished by either changing the shape of the IOL, e.g., to become more convex for near vision focus, or by moving the IOL along its optical axis. For example, a number of these approaches bias an IOL to be located in the most posterior position of the posterior capsular bag of the eye under rest conditions. When near focus is required, the IOL moves forwardly in response to the action of the ciliary muscle of the eye to provide positive accommodation. These approaches often result in insufficient forward axial movement required for full-range accommodation.

In view of the foregoing, it would be beneficial in the art to provide IOLs with enhanced capacity for accommodation.

SUMMARY OF THE INVENTION

The present invention provides new and enhanced holders for intraocular lenses (IOLs) to enhance accommodation of one or more IOLs. Desirably, the holders of the invention also inhibit cell growth, particularly epithelial cell growth, onto the IOL or IOLs retained thereby. The holders of the present invention are straightforward in design and construction, thereby facilitating the manufacturing process, and produce substantial benefits in use in the eye.

According to one aspect of the invention, a holder for an intraocular lens has a holder body that is sized and adapted to be placed in a capsular bag of an eye. The holder body defines a hollow space adapted to receive and retain a fixation member of an IOL. The holder is configured to enhance the accommodation of the IOL in response to contraction and relaxation of the ciliary muscle of the eye. The holder body may be configured to be either separate and apart from the IOL or permanently coupled to the IOL.

According to one useful embodiment of the present invention, the holder body is made from a resilient or compressible material such that the holder body is adapted to cooperate with the eye to facilitate accommodating movement of the intraocular lens. For example, in one embodiment, when the ciliary muscle contracts, the zonules relax and reduce the equatorial diameter of the capsular bag, thereby compressing the holder body and moving the lens therein anteriorly along the optical axis of the eye. This anterior movement of the lens increases or amplifies the amount of positive (i.e., near) accommodation of the lens. Conversely, when the ciliary muscle relaxes, the zonules constrict and increase the equatorial diameter of the capsular bag, thereby allowing the holder body to expand and return to an unstressed shape, which moves the lens posteriorly along the optical axis.

The holder body of the invention may take on a number of specific configurations. For example, the holder body may be circular and shaped like a tire with a peripheral wall and a pair of opposing side walls together defining an annular channel therewithin. Alternatively, the holder body may be C shaped. To enhance collapsibility when the equatorial diameter of the capsular bag is reduced, for example, when the ciliary muscle contracts, the holder body may include a plurality of voids, such as notches formed in the opposing side walls.

One of advantages of the invention results from particularly-shaped annular intersections between the peripheral wall and the pair of opposing side walls. More specifically, to inhibit cell growth along onto the lens, the intersections between the peripheral wall of the holder body and the side walls are substantially discontinuous. For example, the side walls may be disposed substantially perpendicularly to the peripheral wall. Alternatively, the side walls may angulate outwardly from the peripheral wall, e.g., at an angle of up to about 45°. In either embodiment, the peripheral intersection may be considered sharp or abrupt and is effective in inhibiting migration or growth of cells from the eye onto the IOL.

The present invention also provides holders for retaining more than one IOL. According to this aspect of the present invention, the holder body defines an additional hollow space adapted to receive and retain a distal end portion of an additional fixation member of second intraocular lens. Preferably, the holder body includes a spacer member adapted to maintain the fixation member of the first IOL spaced apart from the fixation member of the second IOL.

In one of the useful embodiments of the multi-IOL holders of the invention, an annular ring is disposed in one of the hollow spaces. Accordingly, the inner diameter of one of the hollow spaces is less than that of the other hollow space. Accordingly, the present holders may hold and retain IOLs of different size. In addition, the multi-IOL holder body is adapted to cooperate with the eye to facilitate accommodating movement of at least one of the intraocular lenses retained thereby.

One of the advantages of the retaining lenses of different size is that the holder of the present invention is able to compensate for capsule size variations and to shift the axial position of a dynamic accommodating lens. By shifting the axial position of the dynamic accommodating lens, axial movement is maximized, and hyperopic refractive errors are avoided. The annular ring may also be used to correct axial position errors in either the one-lens or the two-lens system.

Any and all of the features described herein and combinations of such features are included within the scope of the present invention provided that the features of any such combination are not mutually inconsistent.

Additional aspects, features, and advantages of the present invention are set forth in the following description and claims, particularly when considered in conjunction with the accompanying drawings in which like parts bear like reference numbers.

BRIEF DESCRIPTION OF THE DRAWINGS

FIG. 3A is a plan view of a holder for an IOL according to an exemplary embodiment of the invention.

FIG. 3B is a plan view of a discontinuous holder for an IOL according to another exemplary embodiment of the invention.

FIG. 3C is a plan view of a more compressible holder for an IOL according to still another exemplary embodiment of the invention.

FIG. 4 is a cross-sectional view of a holder for multiple IOLs in accordance with an exemplary embodiment of the present invention.

FIG. 5 is a cross-sectional view of a holder for multiple IOLs-of different diameters in accordance with another embodiment of the invention.

FIG. 6 is a cross-sectional view of a holder having a spacer for multiple IOLs in accordance with still another embodiment of the invention.

FIG. 7 is an elevational cross-sectional view of a multiple IOL system within a capsular bag of an eye including an annular spacer.

FIG. 8 is a cross-sectional view of an alternative spacer for use in a multiple IOL system of the present invention.

DETAILED DESCRIPTION OF THE DRAWINGS

Figure 1:
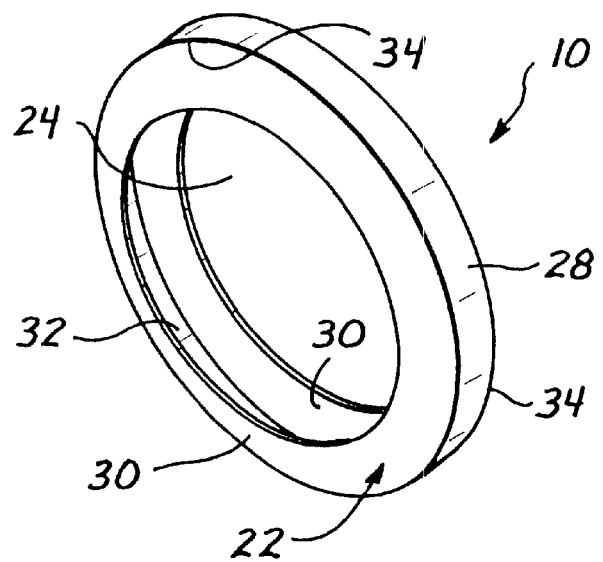
FIG. 1 is a perspective view of a holder for an intraocular lens (IOL) according to an exemplary embodiment of the present invention.
Figure 2:
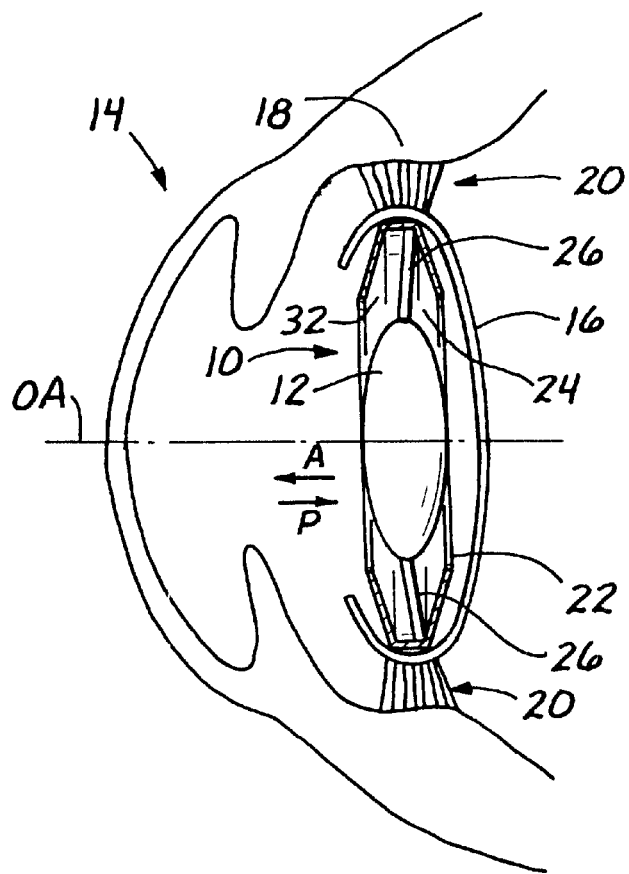
FIG. 2 is a fragmentary cross-sectional view of an eye in which an IOL within the holder of FIG. 1 has been implanted.

Referring to FIGS. 1 and 2, a holder, generally indicated with reference numeral 10, for an intraocular lens (IOL) 12 is illustrated according to an exemplary embodiment of the present invention. The holder 10 receives and retains the IOL 12 located in an eye 14 along an optical axis OA such that the IOL 12 focuses light on the retina (not shown) of the eye.

Briefly describing the anatomy of the mammalian eye 14, a capsular bag 16 is connected to ciliary muscle 18 by suspensory ligaments or zonules 20. In the natural eye, the capsular bag 16 defines the cover or external surface of the lens. The ciliary muscle 18 is the prime mover in accommodation, i.e., in adjusting the eye 14 to focus on near objects. The zonules 20 retain the lens in position and are relaxed by the contraction of the ciliary muscle 18, thereby allowing a natural crystalline lens to become more convex.

Regarding the present invention in more detail, and with reference to FIGS. 1 and 2, exemplary holder 10 has an annular holder body 22 which is sized and shaped to be placed within the capsular bag 16 of the eye 14 in the inner volume previously occupied by the crystalline lens matter. The holder body 22 is made from a resilient material which renders the body compressible and flexible. Because the zonules 20 remain attached to the capsular bag 16, contraction and extension of the ciliary muscle 18 transmits movement to the holder body 22. The compressible holder 10 thus allows accommodation in the pseudophakic eye, which is discussed in detail below.

The holder body 22 defines a hollow space 24 which is adapted to receive and hold the IOL 12. More particularly, the IOL 12 may include one or more fixation members, for example, haptics 26, each of which has a distal end portion. The hollow space 24 of exemplary holder 10 is adapted to receive and retain the IOL, with the distal end portions of the fixation members or haptics 26 extending outward into contact with the holder body 22. It should be understood that the fixation members 26 may be plate-type members, or loop-type members as shown.

Applying the dynamics of the eye 14 to the present invention, exemplary holder 10 facilitates movement of the lens 12 in response to the action of the ciliary muscle 18 and the zonules 20. When near vision is needed, the ciliary muscle 18 contracts, and the zonules 20 relax and reduce the equatorial diameter of the capsular bag 16, thereby compressing the holder 10 and moving the lens 12 anteriorly along optical axis OA as indicated by arrow A in FIG. 2. This anterior movement of the lens 12 increases or amplifies the amount of positive (i.e., near) accommodation of the lens 12. Conversely, when the ciliary muscle 18 relaxes, the zonules 20 constrict and increase the equatorial diameter of the capsular bag 16, thereby allowing the holder 10 to expand and return to an unstressed shape and moving the lens 12 posteriorly along optical axis OA as indicated by arrow P.

With continued reference to FIGS. 1 and 2 and additional reference to FIG. 3A, the holder 10 according to one of the exemplary embodiments of the invention is substantially tire shaped, wherein the annular body 22 has an inner diameter $d_i$, and the peripheral wall 28 has an outer diameter $d_o$. The body 22 has a generally axially-extending peripheral wall 28 and opposing side walls 30 angled away from each other and toward the optical axis OA to define a peripheral annular channel 32 of the hollow space 24. The channel 32 receives and retains the distal end portions of the fixation members 26 of the lens 12.

The ring-shaped holder 10 of the present invention is preferably made from a single piece of moldable biocompatible material. The IOL 12 may be either integral with (i.e., molded with) or mechanically coupled to the holder 10. In a preferred embodiment, the holder 10 is a separate molded part that can be separately implanted in capsular bag 16, and the IOL 12 is inserted, in turn, within the holder.

Exemplary ring-shaped holder 10 dynamically enhances accommodation of the lens 12 by providing substantially complete or 360° supportive contact within the capsular bag 16. Accordingly, any constriction or expansion of the capsular bag 16 is directly and proportionally transferred to the holder 10 for a corresponding action and amplitude upon the lens 12. This substantially complete or 360° interface between the capsular bag 16 and the IOL 12 is in contrast to the multiple points of contact between the fixation members of an IOL and capsular bag without the holder 10. In addition, as the capsular bag 16 atrophies or collapses when the natural crystalline lens is removed, the ring-shaped holder 10 provides enhanced support to maintain the capsular bag in its natural configuration.

To prevent the growth of cells onto the IOL 12, which inhibits posterior capsule opacification (PCO), the peripheral wall 28 preferably shares a respective outer corner edge 34 (FIG. 1) with each of the side walls or walls 30 that is substantially discontinuous or angular. The sharp outer corner edges 34 substantially retard or prevent the growth of cells onto the side walls 30, which growth might eventually extended to the IOL 12.

Particularly referencing FIG. 2, the fixation members 26 of the lens 12 are shown extending outward to be retained within the peripheral channel 32 of the hollow space 24. If the holder 10 and IOL 12 are separate, the IOL can be changed. More specifically, with the holder 10 implanted in the eye 14 and retaining a lens 12, if desired, the lens 12 may be removed from the channel 32 and replaced with another lens. As shown, the side walls 30 may be angulated outwardly from each other while maintaining the outer edges 34 with the preferable substantial discontinuity. For example, the side walls 30 may be angled by up to about 45° with respect to the peripheral wall 28 to provide the abrupt peripheral discontinuity at the outer edges 34. The angle of the anterior side walls 30 facilitates implantation and removal of IOLs 12 from the holder 10.

Rather than being configured as an integral 360 ring as shown in FIGS. 1 and 3A, the holder of the present invention may be configured as a partial ring as shown in FIG. 3B and indicated with reference numeral 110. For the purposes of this description, elements of exemplary holder 110 that are analogous to elements of the holder 10 shown in FIG. 1 are indicated with like reference numerals with the addition of a "1" prefix; e.g., holder body 122 is analogous to body 22 of holder 10. The description of these analogous elements will not be repeated. This referencing convention will apply to additional embodiments of the holder of the invention, with each successive embodiment of the holder having an incremental prefix, i.e., 210, 310, etc.

Exemplary holder 110 of the invention is generally annular but discontinuous with a cut-out portion or gap 136 formed in the body 122, thereby defining ends 138 and defining a substantially C-shaped configuration. Accordingly, when the holder 110 is implanted within an eye and the capsular bag constricts, the holder 110 responsively constricts, urging the ends 138 toward each other across the gap 136. In other words, the discontinuous holder 110 more easily constricts relative to the continuous holder 10, all else being equal. In addition, exemplary partial-ring holder 110 is adjustable to capsular bags of different size.

Alternatively, the holder 110 can be discontinuous though the gap 136 may be omitted. For instance, the ends 138 may overlap in a side-by-side configuration, which permits the holder 110 to flex inward. Or, the ends 138 may interact in some manner, such as by a telescopic arrangement, that permits the holder 110 to flex inward yet omits a gap in the holder.

Another more compressible of the IOL holder of the present invention is shown in FIG. 3C and indicated with reference numeral 210. Rather than removing a portion of the circumference of the body 222 as shown in FIG. 3B to facilitate contraction, exemplary holder 210 includes a plurality of inwardly-facing notches 240 formed in the side walls 230, thereby defining a plurality of inwardly-directed teeth 242. In other words, the annular body 222 may have an inner diameter that is non-uniform and ranges from $d_i$ (min) to $d_i$ (max). Analogous to that described above, when the holder 210 is implanted within an eye and the capsular bag constricts or reduces in equatorial diameter, the holder 210 responsively constricts, urging the teeth 242 toward each other across respective notches 240.

The notches 240 thus present voids in the inner periphery of the holder 210 that facilitates constriction or compression of the holder upon the external forces applied by the surrounding capsular bag. Of course, there are numerous ways to facilitate such constriction by providing voids in the otherwise contiguous holder side walls 230. For instance, diamond-shaped or oval-shaped voids may be provided wholly in the side walls 230 without opening to the inner edge, as do the notches 240. In short, the invention contemplates the provision of voids in the holder 210 that weaken the structural resistance of the holder to inward constriction.

In addition to holding a single IOL 12 as shown in FIG. 2, the holders of the present invention may be configured to hold a plurality of IOLs. For example, a holder 310 for receiving and retaining more than one IOL is shown in FIG. 4. As in the earlier embodiments, the holder 310 has an annular holder body 322 with a peripheral wall 328 and a pair of side walls 330. An annular spacer member 346 is positioned within the holder body 322 between a first hollow space 324 for holding a first IOL 312 (shown in phantom line), and a second hollow space adapted to receive and retain a second IOL 345 (also shown in phantom line). More specifically, the first and second hollow spaces 324 and 344 are adapted to receive and retain the distal end portions of fixation members 326, 347 of the respective IOLs 312, 345.

In the illustrated embodiment of FIG. 4, the first and second spaces 324, 344 are symmetrically formed with the spacer member 346 extending along a midplane of the holder 310. In addition, the anterior IOL 312 is shown larger than the posterior IOL 345. It will be apparent to one of skill in the art, however, that the spaces 324, 344 may be of different size, and the two IOLs may be the same size.

The spacer member 346 defines annular channels 332 and 349 of the first and second spaces 324 and 344, respectively. In addition, the spacer member 346 is adapted to maintain fixation members 326 and 347 of the IOLs 312 and 345 respectively received within the annular channels 332 and 349 such that the IOLs 312 and 345 are held in a spaced relationship. Exemplary multi-IOL holder 310 is adapted to cooperate with the eye to facilitate accommodating movement of at least one of the IOLs 312 and 345 received within the hollow spaces 324 and 344.

The IOLs 312 and 345 may both be separate elements to be inserted into the holder 310, or one or both may be formed together with the holder. In a particularly preferred embodiment, the posteriorly-positioned IOL 345 is formed (i.e., molded) together with the holder 310, and the anteriorly-positioned IOL 312 is separately inserted. In this manner, the anterior IOL 312 can be replaced if necessary.

The advantages of a multiple lens system have been disclosed and described in co-pending U.S. application Ser. No. 09/390,380 filed Sep. 3, 1999, the disclosure of which is hereby expressly incorporated by reference. For example, a multiple lens system allows the use of a higher power IOL having greater accommodation amplitude in conjunction with a meniscus, or negative power, IOL to improve the accommodative amplitude of the pseudophakic eye.

Another embodiment of a multi-IOL holder 410 of the invention is illustrated in FIG. 5. Analogous to the 3.embodiment described above, each of the spaces 424 and 444 has an annular channel 432 and 449, respectively, adapted to receive and retain fixation members 426 and 447 of respective lenses 412 and 445.

In contrast to the symmetric configuration of the spaces 324 and 344 of holder 310 of FIG. 4, exemplary holder 410 has differently dimensioned first and second hollow spaces 424 and 444 separated by an annular spacer member 446 to respectively hold IOLs 412 and 445 (both of which are shown in phantom line). More specifically, exemplary holder 410 may include an annular ring 448 disposed in one of the hollow spaces, e.g., the second space 444, so that the inner diameter of the second space 444 (indicated by $d_2$) is less than the inner diameter of the first space 424 (indicated by $d_1$).

Accordingly, exemplary holder 410 is configured to hold IOLs 412 and 445 of different size. For example, lens 445 having a smaller diameter than lens 412 may be received within the smaller space 444 to compensate for capsule size variations and to shift the axial position of a dynamic accommodating lens to maximize the axial movement and avoiding hyperopic refractive errors. The annular ring 448 may also be provided to correct axial position errors in either a one-lens or a two-lens system.

As shown in FIG. 5, rather than angulating the side walls as described above, side walls 430 of holder 410 are disposed substantially perpendicularly with respect to peripheral wall 428 and optical axis OA, thereby providing 90° outer edges 434.

Yet another exemplary embodiment of a holder 510 of the present invention is shown in FIG. 6. Exemplary holder 510 includes first and second hollow spaces 524 and 544 separated by an annular spacer member 546. In contrast to the relatively thin spacer members described above, the spacer member 546 of exemplary holder 510 has a relatively large maximum thickness t in comparison to the respect axial thickness of the spaces 524 and 544. In addition, sides 550 of the spacer member 546 may taper either outwardly, as shown in FIG. 6, or inwardly. The spacer member 546 thereby defines an increased axial space 552 that allows for substantial axial accommodating movement of the lenses in multiple lens systems toward each other, thereby preventing negative hyperopic events.

For human implantation, the holder 10 (or 110, 210, 310, 410, or 510) may be configured such that the amount of positive or near accommodation of a lens is preferably at least about 1 diopter and may range up to about 3.5 diopters or more. Further, the holders 10 (or 110, 210, 310, 410, or 510) may be configured to provide at least about 1.5 mm or about 2 mm of axial movement of a lens anteriorly in the eye with a reduction of about 1 mm in the equatorial diameter of the capsular bag 16 caused by the ciliary muscle 18 and the zonules 20. Each lens retained by the holders may be a refractive or a diffractive lens body.

The holders of the present invention, as well as each lens retained thereby, may be constructed of rigid biocompatible materials such as polymethyl methacrylate (PMMA) or deformable materials such as silicone polymeric materials, acrylic polymeric materials, hydrogel polymeric materials, and the like. The deformable materials allow the holder 10 (or 110, 210, 310, 410, or 510) to be rolled or folded for insertion through a small incision into the eye. The material or materials of construction from which the holders are made are chosen to provide the holders with the desired mechanical properties, e.g., strength and deformability, to meet the needs of the particular application involved.

The holder 10 (or 110, 210, 310, 410, or 510) may be inserted into the capsular bag 16 of a mammalian eye using conventional equipment and techniques, for example, after the natural crystalline lens is removed, such as by using a phaceomulsification technique. The holder 10 (or 110, 210, 310, 410, or 510) is preferably rolled or folded prior to insertion into the eye to be insertable through a small incision, for example, on the order of about 3.2 mm. After insertion, the holder 10 may be positioned in the eye as shown in FIG. 2.

If the holder 10 (or 110, 210, 310, 410, or 510) is to be implanted in an adult human eye, each lens 12 retained thereby preferably has a diameter in the range of about 3.5 mm to about 7 mm, and more preferably in the range of about 5 mm to about 6 mm. Further, the IOL 10 may have an overall diameter, with the movement assembly 14 in an unstressed condition, of about 8 mm to about 11 mm or about 12 mm. Additionally, the lens 12 preferably has a far-vision correction power for infinity in an accommodated state.

The present invention provides holders that enable accommodation and methods for using such holders. The holders of the invention are configured to reduce the stretching of the capsular bag, to maintain the elasticity and/or integrity of the capsular bag, to enhance the effectiveness of the eye, particularly the function of the ciliary muscle and the zonules. The present holders promote the secure retention within the capsular bag. In addition, the present holders inhibit PCO. These benefits are obtained with holders for IOLs which are streamlined in construction and relatively easy to manufacture and insert into the eye and which effectively provide accommodation for long-term use.

FIG. 7 illustrates a further multiple IOL system 600 of the present invention including a first or anterior IOL 602, a second or posterior IOL 604, and an intermediate spacer 606 therebetween. More specifically, the first IOL 602 includes one or more fixation members 608 that extend radially outward from an optical axis OA into contact with the surrounding capsular bag 610. Likewise, the second IOL 604 has one or more fixation members 612 that extend outward into contact with the capsular bag 610. The spacer member 606 fits closely within the capsular bag 610 between the respective fixation members 608, 612 of the first and second IOLs 602, 604.

In an exemplary embodiment, the spacer member 606 is annular and has an outer periphery 620 and an inner periphery 622. A hollow, preferably cylindrical, space 624 is defined within the inner periphery 622. The hollow space 624 is desirably slightly larger than the lenses of the IOLs 602, 604 to avoid contact therewith. As seen in cross-section, the inner periphery 622 is larger in the axial dimension than and tapers outwardly to the outer periphery 620. Although not shown, the corner edges of the inner periphery 622 of the spacer member 606 are desirably rounded to help reduce wear on the moving IOLs, while the edges of the outer periphery 620 are desirably sharp to inhibit cell growth along the spacer member which otherwise might result in posterior capsular opacification of the IOLs 602, 604.

By providing a solid spacer member between the respective fixation members 608, 612, a minimum separation distance between the two IOLs 602, 604 is maintained which avoids unwanted hyperopic outcomes. More particularly, some multiple IOL systems of the prior art are subject to axial position errors because of a non-uniform shape of the outer capsular bag 610, or from migratory or transient dynamic forces imparted on the lenses. The spacer 606 insures a minimum separation distance between the two-lens system, and therefore attenuates these problems.

FIG. 8 illustrates an alternative spacer member 630 which can be used in place of the spacer member 606 seen in FIG. 7. Instead of tapering outward, the spacer member 630 as an outer periphery 632 that is larger than and tapers inwardly to an inner periphery 634.

The spacer members 606 and 630 of FIGS. 7 and 8 may be annular and continuous, or may be discontinuous for greater flexibility. Indeed, the shape of the spacer members 606 and 630 may be as was described above for the holders of the present invention and seen in FIGS. 3A–3C.

While the present invention has been described with respect to various specific examples and embodiments, it is to be understood that the invention is not limited thereto and that it can be variously practiced within the scope of the following claims.

What is claimed is:

1. A holder for an intraocular lens located in an eye, the holder comprising:
    a holder body sized and adapted to be placed in a capsular bag of a mammalian eye;
    the holder body defining a hollow space adapted to receive and retain a distal end portion of a fixation member of an intraocular lens, the holder body providing an interface between the capsular bag and the fixation member; and
    the holder body has an inner periphery and an outer periphery, and the holder body has an inner diameter that is non-uniform along a circumference of the inner periphery that is perpendicular to a central longitudinal axis of the holder to reduce structural resistance of the holder to inward forces imposed by the eye.

2. The holder of claim 1 wherein the holder body is made from a resilient material.

3. The holder of claim 1 wherein the holder body is generally annular.

4. The holder of claim 1 wherein the one or more voids comprise a plurality of notches.

5. The holder of claim 1 wherein the holder body includes a peripheral wall and a pair of opposing side walls attached to the peripheral wall and extending generally radially inwardly from the peripheral wall.

6. The holder of claim 5 wherein at least one of the side walls angle away from the other in a radially inwardly direction.

7. The holder of claim 1 wherein the holder body defines a second hollow space adapted to receive and retain a distal end portion of a fixation member of a second intraocular lens.

8. The holder of claim 7 wherein the holder body includes a spacer member adapted to maintain the fixation member of the first intraocular lens spaced apart from the fixation member of the second intraocular lens.

9. The holder of claim 8 which further comprises a structure sized and positioned to reduce the size of one of the hollow spaces.

10. The holder of claim 9 wherein the structure includes a ring held within the holder body to reduce a diameter of one of the hollow spaces.

11. The holder of claim 7 wherein the holder body is adapted to cooperate with the eye to facilitate accommodating movement of at least one of the first and second intraocular lenses.

12. The holder of claim 1 wherein the holder body is adapted to cooperate with the eye to facilitate accommodating movement of the intraocular lens.

13. The holder of claim 1 wherein the holder body includes at least one outer corner edge formed at a discontinuity.

14. The holder of claim 13 wherein cell growth from the eye onto the optic of the intraocular lens is reduced relative to a similar intraocular lens held by a similar holder without the at least one outer corner edge.

15. A holder for an intraocular lens located in an eye, the holder comprising:
    a holder body sized and adapted to be placed in a capsular bag of a mammalian eye;
    the holder body defining a first hollow space adapted to receive and retain a distal end portion of a fixation member of a first intraocular lens and a second hollow space adapted to receive and retain a distal end portion of a fixation member of a second intraocular lens, the holder body providing an interface between the capsular bag and the fixation members of the first and second intraocular lenses, and including a spacer member adapted to maintain the fixation member of the first intraocular lens spaced apart from the fixation member of the second intraocular lens; and
    the holder including a structure that reduces the size of one of the first and second hollow spaces.

16. The holder of claim 15 wherein the holder body is made from a resilient material and is generally annular.

17. The holder of claim 15 wherein the structure includes a ring held within the holder body to reduce a diameter of one of the hollow spaces.

18. The holder of claim 15 wherein the holder body is adapted to cooperate with the eye to facilitate accommodating movement of at least one of the first and second intraocular lenses.

19. A holder for an intraocular lens located in an eye, the holder comprising:
    a holder body sized and adapted to be placed in a capsular bag of a mammalian eye;
    the holder body defining a first hollow space adapted to receive and retain a distal end portion of a fixation member of an intraocular lens, the holder body providing an interface between the capsular bag and the fixation member; and
    the holder body including a continuous outer peripheral wall and a pair of opposing side walls attached to the outer peripheral wall and extending generally radially inwardly from the peripheral wall, wherein the peripheral wall and at least one of the side walls intersect at a discontinuity.

20. The holder of claim 19 wherein the holder body is made from a resilient body and is generally annular.

21. The holder of claim 19 wherein the holder body includes voids that reduce the structural resistance of the holder to inward forces imposed by the eye.

22. The holder of claim 19 which is effective, when placed in the capsular bag of an eye, in inhibiting migration or growth of cells from the eye onto an intraocular lens including a fixation member received and retained in the hollow space.

23. The holder of claim 19 wherein at least one of the side walls angles away from the other in a direction radially inwardly from the peripheral wall.

24. The holder of claim 19 wherein the holder body defines a second hollow space adapted to receive and retain a distal end portion of a fixation member of a second intraocular lens.

25. The holder of claim 24 wherein the holder body includes a spacer member adapted to maintain the fixation member of the first intraocular lens spaced apart from the fixation member of the second intraocular lens.

26. The holder of claim 19 wherein the holder body is adapted to cooperate with the eye to facilitate accommodating movement of the intraocular lens.

27. An intraocular lens system comprising:
    a first intraocular lens including at least one fixation member;
    a second intraocular lens including at least one fixation member;
    a spacer member separate and apart from both the first and second intraocular lenses and positioned between the at least one fixation member of the first and second intraocular lenses to maintain a spacing therebetween; and
    a peripheral annular ring defining a hollow space therein and substantially enclosing the fixation members of the first and second intraocular lenses.

28. The system of claim 27 wherein the peripheral annular ring has a peripheral wall and a pair of opposing side walls attached to the peripheral wall and extending radially inwardly from the peripheral wall.

29. The system of claim 28 wherein at least one of the side walls angle away from the other in a radially inwardly direction.

30. The system of claim 27 wherein the annular ring is sized to be implanted in a capsular bag of an eye and includes voids that reduce the structural resistance of the ring to inward forces imposed by the eye.

31. The system of claim 30 wherein the annular ring has an outer periphery and an inner periphery, and the voids are provided on the inner periphery as a plurality of notches.

32. An intraocular lens system comprising:
    a first intraocular lens including at least one fixation member;
    a second intraocular lens including at least one fixation member; and
    a spacer member separate and apart from both the first and second intraocular lenses and positioned between the at least one fixation member of the first intraocular lens and the at least one fixation member of the second intraocular lens to maintain spacing therebetween, the spacer member including an outer peripheral wall and a pair of opposing side walls attached to an outer peripheral wall and extending generally radially inwardly from the outer peripheral wall, wherein the outer peripheral wall and at least one of the side walls intersect at a discontinuity.

33. The system of claim 32 wherein the spacer member is annular and has a trapezoidal radial cross-section.

34. The system of claim 33 wherein the spacer member has an outer periphery and an inner periphery and wherein the trapezoidal radial cross-section tapers from the outer periphery to the inner periphery.

35. The system of claim 32 wherein the spacer member is effective in inhibiting migration or growth of cells from an eye in which the system is placed onto the first and second intraocular lenses.

36. The holder of claim 1 wherein the holder body includes one or more voids on the inner periphery.

37. A holder for an intraocular lens located in an eye, the holder comprising:
    a holder body sized and adapted to be placed in a capsular bag of a mammalian eye;
    the holder body defining a hollow space adapted to receive and retain a distal end portion of a fixation member of an intraocular lens, the holder body providing an interface between the capsular bag and the fixation member; and
    the holder body has an inner periphery and an outer periphery, and includes a plurality of notches on the inner periphery to reduce structural resistance of the holder to inward forces imposed by the eye.

38. The holder of claim 37 wherein the holder is made from a resilient material.

39. The holder of claim 37 wherein the holder body includes a peripheral wall and a pair of opposing side walls attached to the peripheral wall and extending generally radially inwardly from the peripheral wall.

40. The holder of claim 37 wherein the holder body defines a second hollow space adapted to receive and retain a distal end portion of a fixation member of a second intraocular lens.

41. The holder of claim 40 wherein the holder body includes a spacer member adapted to maintain the fixation member of the first intraocular lens spaced apart from the fixation member of the second intraocular lens.

42. The holder of claim 37 wherein the holder body includes at least one outer corner edge formed at a discontinuity.

43. The holder of claim 42 wherein cell growth from the eye onto an optic of the intraocular lens held by the holder is reduced relative to a similar intraocular lens held by a similar holder without the at least one outer corner edge.

44. A holder for an intraocular lens located in an eye, the holder comprising:
    a holder body sized and adapted to be placed in a capsular bag of a mammalian eye;
    the holder body defining a hollow space adapted to receive and retain a distal end portion of a fixation member of an intraocular lens, the holder body providing an interface between the capsular bag and the fixation member; and
    the holder body has an inner periphery and an outer periphery, and includes one or more voids on the inner periphery to reduce structural resistance of the holder to inward forces imposed by the eye, and includes at least one outer corner edge formed at a discontinuity.

45. The holder of claim 44 wherein cell growth from the eye onto an optic of the intraocular lens held by the holder is reduced relative to a similar intraocular lens held by a similar holder without the at least one outer corner edge.

46. The holder of claim 44 wherein the one or more voids comprise a plurality of notches.

* * * * *